US008143444B2

(12) United States Patent
Mariansky et al.

(10) Patent No.: US 8,143,444 B2
(45) Date of Patent: Mar. 27, 2012

(54) RECOVERY OF ORGANIC ACIDS

(75) Inventors: Gal Mariansky, San Francisco, CA (US); Kevin Carlin, Oakland, CA (US); Dan W. Verser, Menlo Park, CA (US)

(73) Assignee: ZeaChem, Inc., Menlo Park, CA (US)

( * ) Notice: Subject to any disclaimer, the term of this patent is extended or adjusted under 35 U.S.C. 154(b) by 246 days.

(21) Appl. No.: 12/437,445

(22) Filed: May 7, 2009

(65) Prior Publication Data
US 2009/0281354 A1 Nov. 12, 2009

Related U.S. Application Data

(60) Provisional application No. 61/051,243, filed on May 7, 2008.

(51) Int. Cl.
C07C 51/42 (2006.01)

(52) U.S. Cl. ........................................ 562/600; 562/608

(58) Field of Classification Search .................. 562/600, 562/608
See application file for complete search history.

(56) References Cited

U.S. PATENT DOCUMENTS

| | | |
|---|---|---|
| 1,421,605 A | 7/1922 | Steffens |
| 4,055,590 A | 10/1977 | Gruber et al. |
| 4,100,189 A | 7/1978 | Mercier |
| 4,113,662 A | 9/1978 | Wall |
| 4,275,234 A | 6/1981 | Baniel et al. |
| 4,282,323 A | 8/1981 | Yates |
| 4,353,784 A | 10/1982 | Koga et al. |
| 4,379,028 A | 4/1983 | Berg et al. |
| 4,405,717 A | 9/1983 | Urbas |
| 4,407,954 A | 10/1983 | Clyde |
| 4,444,881 A | 4/1984 | Urbas |
| 4,569,726 A | 2/1986 | Berg et al. |
| 4,698,303 A | 10/1987 | Bailey et al. |
| 4,771,001 A | 9/1988 | Bailey et al. |
| 4,830,963 A | 5/1989 | Brumm et al. |
| 4,935,360 A | 6/1990 | Klemps et al. |
| 5,068,188 A | 11/1991 | Wise et al. |
| 5,071,754 A | 12/1991 | Walkup et al. |
| 5,137,818 A | 8/1992 | Harder et al. |
| 5,210,296 A | 5/1993 | Cockrem et al. |
| 5,412,126 A | 5/1995 | King et al. |
| 5,424,202 A | 6/1995 | Ingram et al. |
| 5,453,365 A | 9/1995 | Sterzel et al. |
| 5,510,526 A | 4/1996 | Baniel et al. |
| 5,563,069 A | 10/1996 | Yang |
| 5,599,976 A | 2/1997 | Scates et al. |
| 5,620,877 A | 4/1997 | Farone et al. |
| 5,723,639 A | 3/1998 | Datta et al. |
| 5,766,439 A | 6/1998 | Eyal et al. |
| 5,773,653 A | 6/1998 | Baniel |
| 5,780,276 A | 7/1998 | Baniel |
| 5,874,263 A | 2/1999 | Holtzapple et al. |
| 5,986,133 A | 11/1999 | Holtzapple et al. |
| 6,136,577 A | 10/2000 | Gaddy |
| 6,160,173 A | 12/2000 | Eyal et al. |
| 6,262,313 B1 | 7/2001 | Holtzapple et al. |
| 6,284,904 B1 | 9/2001 | Ponnampalam |
| 6,368,819 B1 | 4/2002 | Gaddy et al. |
| 6,395,926 B1 | 5/2002 | Holtzapple et al. |
| 6,478,965 B1 | 11/2002 | Holtzapple et al. |
| 6,509,180 B1 | 1/2003 | Verser et al. |
| 6,926,810 B2 | 8/2005 | Cockrem et al. |
| 6,927,048 B2 | 8/2005 | Verser et al. |
| 7,074,603 B2 | 7/2006 | Verser et al. |
| 7,309,602 B2 | 12/2007 | David |
| 7,351,559 B2 | 4/2008 | Verser et al. |
| 7,507,562 B2 | 3/2009 | Verser et al. |
| 7,601,865 B2 | 10/2009 | Verser et al. |
| 7,682,812 B2 | 3/2010 | Verser et al. |
| 2005/0112739 A1 | 5/2005 | Golubkov |
| 2006/0024801 A1 | 2/2006 | Holtzapple et al. |
| 2006/0222585 A1 | 10/2006 | Verser et al. |
| 2007/0014895 A1 | 1/2007 | Holtzapple et al. |
| 2008/0102502 A1 | 5/2008 | Foody et al. |
| 2008/0176301 A1 | 7/2008 | Granda et al. |
| 2008/0193989 A1 | 8/2008 | Verser et al. |
| 2008/0248540 A1 | 10/2008 | Yang |
| 2008/0280338 A1 | 11/2008 | Hall et al. |
| 2009/0081749 A1 | 3/2009 | Verser et al. |
| 2009/0203098 A1 | 8/2009 | Verser |
| 2010/0120104 A1 | 5/2010 | Reed |

FOREIGN PATENT DOCUMENTS

GB 933714 8/1963

(Continued)

OTHER PUBLICATIONS

International Preliminary Report on Patentability for International (PCT) Patent Application No. PCT/US2009/043188, mailed Nov. 18, 2010.

(Continued)

Primary Examiner — Jafar Parsa
(74) Attorney, Agent, or Firm — Sheridan Ross P.C.

(57) ABSTRACT

A method is disclosed for the recovery of an organic acid from a dilute salt solution in which the cation of the salt forms an insoluble carbonate salt. An amine and $CO_2$ are introduced to the solution to form the insoluble carbonate salt and a complex between the acid and the amine. The acid/amine complex is thermally dissociated, or "cracked", in the presence of a water immiscible solvent in which the amine is selectively soluble and in which the acid is not appreciably soluble. The organic acid may then be recovered from the water by any suitable means such as distillation, reactive distillation, extraction, or reactive extraction.

50 Claims, 6 Drawing Sheets

FOREIGN PATENT DOCUMENTS

| | | |
|---|---|---|
| JP | S59-29633 | 2/1984 |
| JP | 11-503514 | 3/1999 |
| WO | WO 82/03854 | 11/1982 |
| WO | WO 83/03409 | 10/1983 |
| WO | WO 93/00440 | 1/1993 |
| WO | WO 99/00352 | 1/1999 |
| WO | WO 99/00512 | 1/1999 |
| WO | WO 00/53791 | 9/2000 |
| WO | WO 2006/007406 | 1/2006 |
| WO | WO 2007/009085 | 1/2007 |
| WO | WO 2008/070561 | 6/2008 |

OTHER PUBLICATIONS

U.S. Appl. No. 12/511,526, filed Jul. 29, 2009, Verser et al.
U.S. Appl. No. 12/548,312, filed Aug. 26, 2009, Verser et al.
U.S. Appl. No. 12/693,533, filed Jan. 26, 2010, Verser et al.
Busche et al., Biotechnol. Bioeng. Symp., "Recovery of Acetic Acid From Dilute Acetate Solution", No. 12, pp. 249-262 (1982).
Busche, Robert M., Recovering Chemical Products from Dilute Fermentation Broths, Biotechnology and Bioengineering Symp. No. 13, 597-615 (1983).
Buschhorn, H., et al., "Production and utilization of ethanol by the homoacetogen Acetobacterium woodii," Appl. Environ. Microbiol. 55, 1835-1840 (1989).
Drake, "Acetogenesis, Acetogenic Bacteria, and the Acetyl-CoA 'Wood/Ljungdahl' Pathway: Past and Current Perspectives", Acetogenesis, 1994, Chapter 1, pp. 3-60, Chapman and Hall, Inc., New York, NY.
Drake, Acetogenesis, Figure 12.2, 1994, p. 343, Chapman Hall, New York.
Drake, et al, "Old Acetogens, New Light" Ann. NY Acad. Sci. 1125: 100-128 (2008).
Eggeman et al. "Recovery of Organic Acids from Fermentation Broths", Mar. 1, 2005, Applied Biochemistry and Biotechnology, vol. 122, pp. 605-618.
Eggeman Tim et al: "The importance of utility systems in today's biorefineries and a vision for tomorrow" Applied Biochemistry and Biotechnology, vol. 130, No. 1-3, Mar. 2006, pp. 361-381, XP002499935 ISSN: 0273-2289.
Husson et al., Regeneration of Lactic and Succinic Acid-Laden Basic Sorbents by Leaching with a Volatile Base in an Organic Solvent, Ind. Eng. Chem. Res. 37:2996-3005 (1998).
Matar et al. "Chemistry of Petrochemical Processes", Gulf Publishing Company, 1994, cover, contents, p. 162-163.
Miller, Richard W. et al: "Extraction of Lactic Acid from a Calcium Lactate Solution Using Amine-Containing Solvents and Carbon Dioxide Gas. 1. Experimental Procedures" Industrial & Engineering Chemistry Research, 35(4), 1156-62, 1996.
Othmer, "Acetic Acid Recovery Methods", Chemical Engineering Progress, Jul. 1958, pp. 48-59, vol. 54, No. 7.
Pöpken, et al., "Reaction Kinetics and Chemical Equilibrium of Homogeneously and Heterogeneously Catalyzed Acetic Acid Esterification with Methanol and Methyl Acetate Hydrolysis", Industrial and Engineering Chemistry Research, Jun. 17, 2000, pp. 2601-2611, vol. 39, No. 7.
Reisinger et al., Extraction and Sorption of Acetic Acid at pH above pKa to Form Calcium Magnesium Acetate, Ind. Eng. Chem. Res., 34:845-852 (1995).
Ricker et al., Solvent Extraction With Amines for Recovery of Acetic Acid From Dilute Aqueous Industrial Streams, J. Separ. Proc. Technol., 1(2):23-30 (1980).
Ricker, et al., "Solvent Properties of Organic Bases for Extraction of Acetic Acid from Water", Journal of Separation Process Technology, 1979, pp. 36-41, vol. 1, No. 1.
Saha, et al., "Recovery of dilute acetic acid through esterification in a reactive distillation column", Catalysis Today, 2000, pp. 147-157, vol. 60.
Tamada et al., Extraction of Carboxylic Acids with Amine Extractants. 3. Effect of Temperature, Water Coextraction, and Process Considerations, Ind. Eng. Chem. Res. 29:1333-1338 (1990).
Wardell et al., Solvent Equilibria for Extraction of Carboxylic Acids from Water, Journal of Chemical and Engineering Data, 23(2):144-148 (1978).
International Search Report for International (PCT) Patent Application No. PCT/US2009/043188, mailed Jun. 16, 2009.
Written Opinion for International (PCT) Patent Application No. PCT/US2009/043188, mailed Jun. 16, 2009.
Xin et al., "Recovery of acetic acid from waste water," Chemical Engineering (China), Oct. 25, 1996, vol. 24(5), pp. 41-44 (including translated abstract).

RECOVERY OF ORGANIC ACIDS

CROSS-REFERENCE TO RELATED APPLICATIONS

The present application claims priority from U.S. Provisional Patent Application Ser. No. 61/051,243, filed May 7, 2008, which is incorporated herein by reference in its entirety.

FIELD OF THE INVENTION

The present invention is related to methods for recovery of organic acids from dilute salt solutions, such as fermentation broths.

BACKGROUND OF THE INVENTION

In the production of organic acids, such as acetic acid, lactic acid, etc., by fermentation it is usually required to neutralize the fermentation as it proceeds so that the pH does not fall too far and inhibit the fermentation organism. Many fermentations operate optimally near neutral pH. This pH control is usually carried out by the addition of a base such as NaOH or $Ca(OH)_2$ to the fermentor. This means that the product of the fermentation is a dilute salt, such as sodium acetate or calcium acetate, of the organic acid, not the free acid itself. Therefore, if it is desired to recover the free acid, it is necessary to convert the salt back to the acid and separate the acid from the dilute aqueous broth.

Many methods have been proposed to address this problem. Among the simplest methods is the addition of a strong mineral acid, such as sulfuric acid, to the broth containing the organic acid salt. Because the sulfuric acid is a much stronger acid than the organic acids, it shifts the ionic equilibrium so that essentially all of the organic acid salt is converted to the free acid. However, the strong acid is itself simultaneously converted to a salt. If the salt is not useful it can be disposed of, but this is often an economic and environmental burden since the byproduct salt is produced in an equal molar amount as the organic acid.

Other methods have been proposed to recover the organic acid from the dilute salt solution. One of the more interesting is the use of an amine to convert the alkaline metal salt to an organic salt. For example, Urbas, U.S. Pat. No. 4,405,717, incorporated herein by reference in its entirety, describes the use of tributyl amine (TBA) and $CO_2$ to convert a dilute calcium salt to an insoluble $CaCO_3$ and a water-soluble organic complex of TBA and acetic acid at very high yield. Urbas suggests the extraction of the TBA acid complex from the dilute aqueous solution and then the concentration and "cracking" or thermal decomposition of the recovered organic complex to regenerate the TBA and the acetic acid. However, the thermal cracking of the concentrated complex leads to the creation of intractable byproducts of the TBA such as quaternary salts and "tars." The subsequent loss of TBA is an operational and economic burden.

Verser et al (U.S. Patent Publication No. 2005/0256337), incorporated herein by reference in its entirety, describe the recovery of the acid from the extracted TBA acid complex by forming its ester directly from the extract.

A number of processes have been proposed for extraction and regeneration of amine complexes. King, et al., U.S. Pat. No. 5,412,126, and Baniel, U.S. Pat. No. 4,275,234, describe extraction and regeneration methods. Koga et al. U.S. Pat. No. 4,353,784 extracts with high boiling tertiary amine and distills the acid, similar to King. Wise et al. U.S. Pat. No. 5,068,188 extract with amine and back extract with limestone to make alkaline earth acetate, but this does not regenerate a free acid. Thomas et al published U.S. Patent Application 2006/0024801 A1 where they acidify with a low molecular amine, concentrate by evaporation, replace the low molecular amine with a high molecular amine in a distillation column and distill the acid from the high molecular amine. Datta et al. U.S. Pat. No. 5,723,639 focus mainly on ammonium salt but also claims amine-containing salts in which a light alcohol is added to the dilute salt; the mixture is heated in the presence of a catalyst and subjected to pervaporation with hydrophilic membrane.

Some of these methods depend upon back extraction into water at a different temperature, distillation of the acid, or distillation of the amine. The acid can also be back extracted into an aqueous base solution as in Bailey et al., U.S. Pat. No. 4,771,001.

None of these methods, however, have provided a simple low energy way to recover the dilute acid salt and produce the free organic acid.

SUMMARY OF THE INVENTION

A first method of the present invention is a method to recover organic acids from a dilute salt solution. The dilute salt solution comprises an organic acid salt, the cation of which forms an insoluble carbonate salt. The method includes introducing an amine and $CO_2$ to the dilute salt solution to form an acid/amine complex and the insoluble carbonate salt. The acid/amine complex is heated in the presence of a water immiscible solvent to thermally dissociate the acid/amine complex. The acid is immiscible in the solvent and a solvent phase comprising amine and an aqueous phase comprising acid is formed. The method further separates the solvent phase and aqueous phase.

In one embodiment the step of heating further comprises mixing the solution of the acid/amine complex and the water immiscible solvent. In other embodiments, the step of heating may comprise heating to at least about 110° C., to at least about 170° C. or to between about 120° C. to about 220° C. In various embodiments of the method, the step of heating may be conducted for at least about 5 seconds, for at least about 1 minute or for at least about 5 minutes. In other embodiments of the method, the step of separating the phases can consist of decanting, centrifugation or settling. The method can also comprise recovering the organic acid from the aqueous phase. The step of recovering can be selected from distillation, reactive distillation, extraction and reactive extraction.

In a further embodiment of the method, the water immiscible solvent comprises an aromatic solvent. The water immiscible solvent can be selected from benzene, toluene, xylene, ethyl benzene, mesitylene, cumene or mixtures thereof. The water immiscible solvent of the method may also comprise a normal hydrocarbon solvent, where the hydrocarbon solvent can be selected from hexane, heptane, octane, decane, dodecane, decalin or mixtures thereof. In various embodiments of the method, less than about 1%, less than about 0.5% or less than about 0.1% of the acid is present in the solvent. In other embodiments of the method, the amine is a tertiary amine which can be selected from tributylamine, dicyclohexyl methylamine, di-isopropyl amine or mixtures thereof. The amine from the solvent phase may be used as the amine introduced to the dilute salt solution.

In another embodiment of the method, the organic acid may be produced by fermentation in a fermentation medium. The organic acid of the method may comprise a carboxylic acid. The organic acid of the method can be selected from acetic acid, lactic acid, propionic acid, butyric acid, caproic acid, succinic acid, citric acid, 3-hydroxypropionic acid, glycolic acid, formic acid or mixtures thereof. Preferably, the organic acid of the method may also comprise acetic acid.

A second method of the present invention is a method for the recovery of an organic acid from an amine salt of the organic acid. The method comprises heating an aqueous solvent comprising the amine salt of the organic acid in the presence of a water immiscible solvent to thermally dissociate the amine salt of the organic acid to form an amine and an organic acid. The organic acid of the method is immiscible in the water immiscible solvent.

In one embodiment of the method, the step heating further comprises mixing the aqueous solvent and the water immiscible solvent. The step of heating can comprise of heating to at least about 110° C., to at least about 170° C. or to between 120° C. to about 220° C. The step of heating may be conducted for about 5 seconds, for at least 1 minute or at least about 5 minutes.

The water immiscible solvent comprises an aromatic solvent that may be selected from benzene, toluene, xylene, ethyl benzene, mesitylene, cumene or mixtures thereof. The water immiscible may also comprise a normal hydrocarbon solvent which can be selected from hexane, heptane, octane, decane, dodecane, decalin or mixtures thereof. In a further embodiment of the method, the method comprises separating the aqueous solvent and the water immiscible solvent. The step of separating may be selected from decanting, centrifugation or settling. Another embodiment of the method may comprise recovering the organic acid from the aqueous solvent. The step of recovering the organic acid can be selected from distillation, reactive distillation, extraction or reactive extraction.

In various embodiments of the method, the organic acid was produced by fermentation in a fermentation medium. The organic acid may comprise a carboxylic acid which may be selected from acetic acid, lactic acid, propionic acid, butyric acid, caproic acid, succinic acid, citric acid, 3-hydroxypropionic acid, glycolic acid, formic acid or mixtures thereof. The organic acid may comprise acetic acid. In another embodiment of the method, less than about 1%, less than about 0.5%, less than about 0.1% of the acid is present in the immiscible solvent. In a further embodiment of the method, the amine is a tertiary amine that may be selected from tributylamine, dicyclohexyl methyl amine, di-isopropyl ethyl amine or mixtures thereof.

DETAILED DESCRIPTION OF THE INVENTION

Figure 1:
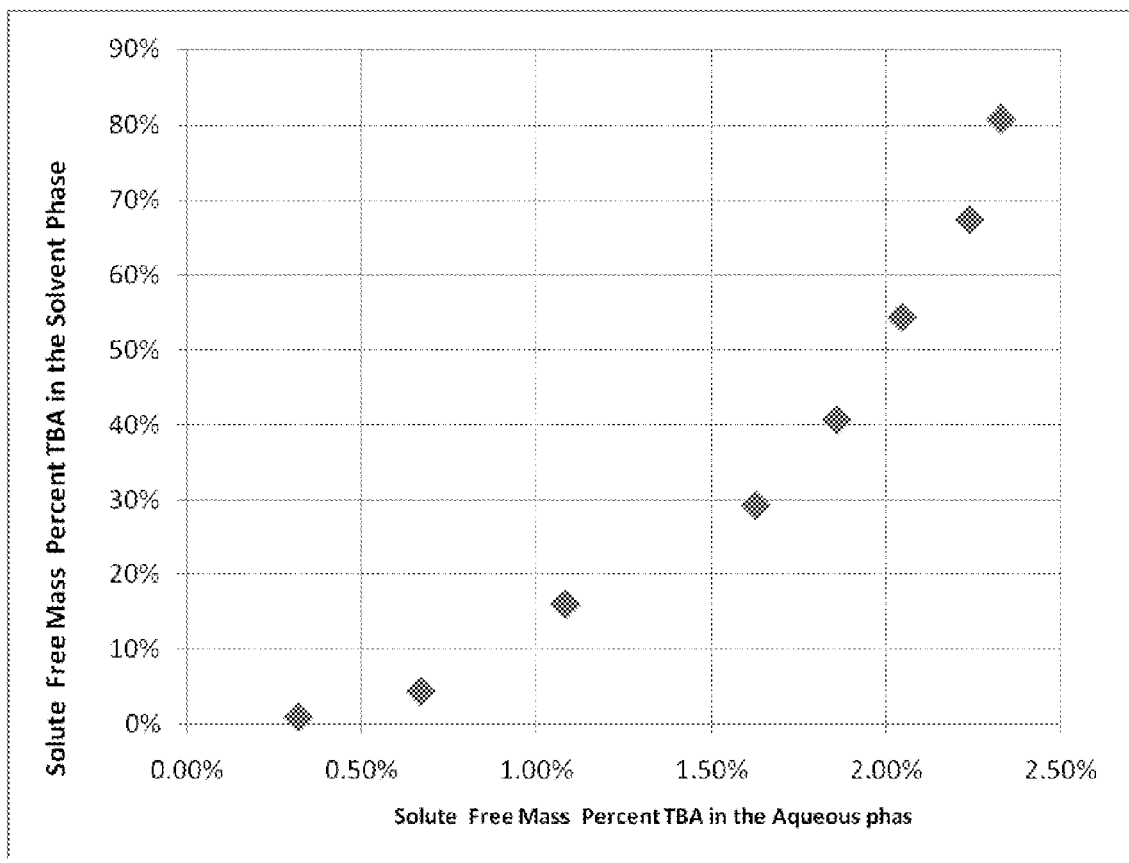
FIG. 1 is a graph illustrating the mass percent of TBA in solvent and aqueous solutions at equilibrium.

The present invention provides for the recovery and separation of organic acids (e.g., carboxylic acids) from a dilute solution such as a fermentation broth, where the organic acids are in the form of salts formed from the reaction of the acid and a base used to neutralize the acid during fermentation for pH control. One example of such an organic acid salt is calcium acetate formed from lime or calcium carbonate and the acetic acid produced by a fermentation organism. For example, if a fermentation producing acetic acid is neutralized with calcium carbonate, the resulting organic acid salt produced in fermentation will be calcium acetate:

2 Acetic Acid+$CaCO_3$→Calcium Acetate+$H_2O$+$CO_2$

One embodiment of the present invention is a method for recovery of an organic acid from a dilute salt solution that comprises an organic acid salt, the cation of which forms an insoluble carbonate salt. This method includes introducing an amine, such as a tertiary amine, and carbon dioxide to the dilute salt solution to form an acid/amine complex and the insoluble carbonate salt. The method further includes heating the acid/amine complex in the presence of a water immiscible solvent to thermally dissociate the acid/amine complex. In this embodiment, the acid is immiscible in the solvent. Upon heating to thermally dissociate the acid/amine complex, the resulting acid stays in the aqueous phase because it is not miscible in the solvent. The dissociation may not be complete and any undissociated acid/amine complex also stays in the aqueous phase. The resulting amine, reports to the solvent because it prefers solvent to the aqueous phase. Thus, the heating step forms a solvent phase comprising amine and an aqueous phase comprising acid. In this manner, the amine in the solvent is effectively sequestered from the acid. Otherwise, if the acid and amine were in proximity, they could reform the acid/amine complex. But, since the acid and the amine are in separate phases, the method can further include separating the solvent phase and the aqueous phase This embodiment of the present invention is particularly suitable for use with organic acids, and particularly carboxylic acids, in dilute salt solutions that are produced by fermentation. For example, such organic acids can include acetic acid, lactic acid, propionic acid, butyric acid, caproic acid, succinic acid, citric acid, 3-hydroxypropionic acid, glycolic acid, formic acid, and mixtures thereof; preferably, includes acetic acid, lactic acid, and propionic acid; and preferably includes acetic acid.

The organic acid salt in this embodiment comprises a cation that forms an insoluble carbonate salt. For example, calcium carbonate is insoluble. Other suitable cations in addition to calcium include zinc, barium, and magnesium.

The organic acid salt is converted to an amine salt by reacting the salt in water with an amine and carbon dioxide, as described, for example, in U.S. Patent Publication No. 2005/0256337, the contents of which are incorporated herein in their entirety. For example:

Ca(Ac)$_2$+$H_2O$+$CO_2$+2TBA=>2TBA:HAc+$CaCO_3$

More specifically, the step of introducing an amine and carbon dioxide to the dilute salt solution is typically conducted at near neutral pH while the solution is mixed with the amine with the carbon dioxide being bubbled through the mixture. In this manner, the organic acid salt reacts with water, carbon dioxide, and the amine to form an acid/amine complex and the insoluble carbonate salt. The carbonate salt will fall out of the solution, thereby driving the reaction in the direction of forming the acid/amine complex, essentially to completion. A significant advantage of the present invention is that this reaction can be conducted under ambient conditions of temperature and pressure and at near neutral pH, such as the pH of a fermentation broth.

Any amine, the acid/amine complex of which is soluble in a dilute salt solution, is suitable for use in this step of the process. In particular, the amine can be a tertiary amine and can be selected from the group consisting of tributyl amine (TBA), dicyclohexyl methyl amine, di-isopropyl ethyl amine and mixtures thereof.

The insoluble alkaline earth metal, such as calcium carbonate, can be easily recovered by conventional solid-liquid separation. For example, calcium carbonate, $CaCO_3$, formed by the reaction of tributyl amine, calcium acetate, water and carbon dioxide can be recycled to the fermentation for pH control. In one embodiment, this salt can be used as a base in an organic acid fermentation for pH control during an initial production of an organic acid. Such use of calcium carbonate during a fermentation produces carbon dioxide which can be used in various embodiments of the invention to form an acid/amine complex and insoluble carbonate salt. In this integrated process, there is not net production of carbon dioxide. Thus, the step of introducing carbon dioxide to a dilute salt solution as an acidulant provides significant advantages because it overcomes the consumption of mineral acid and the issue of salt disposal in the recovery of organic acids. This integrated process is described in U.S. Patent Publication No. 2005/0256337.

One advantage of the present invention is that there is no need to concentrate the amine salt or extract it from the aqueous solution in which it is formed, resulting in a consequent saving in energy. In some embodiments, the amine salt is present in the aqueous solution at a concentration of less than about 15%, less than about 10%, less than about 8%, less than about 5%, or less than about 4% on an acetate basis, where acetate basis is the weight % of acetic acid as a salt (i.e. TBA:Hac or $Ca(AC)_2$).

Suitable water immiscible solvents include those that are immiscible with water and immiscible with the acid. The solvent and the aqueous solution must form two phases at the operating temperature to which the system is heated for the regeneration of the amine. While the solvent must also be miscible with the amine, any solvent that is immiscible with water will be miscible with the amine. In this manner, as the acid/amine complex is thermally dissociated in the presence of a water immiscible solvent, the amine can be sequestered in the solvent to avoid or limit reaction with the acid and reformation of the acid/amine complex. Any solvent that is immiscible with water can be used but preferred solvents dissolve only a small amount of water at higher temperatures. For example, preferred solvents will have less than about 10%, less than about 5%, less than about 1%, or less than about 0.5% by weight water at operating temperatures. Suitable solvents include aromatic solvents, normal hydrocarbon solvents and mixtures thereof. For example, aromatic solvents can include solvents such as benzene, toluene, xylene, ethyl benzene, mesitylene, cumene, and mixtures thereof. Preferred solvents include normal hydrocarbons, which include solvents such as hexane, heptane, octane, decane, dodecane, decalin, and mixtures thereof. Such components, being relatively hydrophobic, are thought to assist by keeping water out of the water immiscible solvent, thereby improving the effective selectivity of the solvent.

The method further includes heating the acid/amine complex in the presence of the water immiscible solvent to thermally dissociate the acid/amine complex. The thermal dissociation, or "cracking", of the acid/amine complex will primarily take place in water but, upon dissociation, a solvent phase comprising amine and an aqueous phase comprising acid are formed. The composition of the dilute salt solution, acid/amine complex and water immiscible solvent can be heated to any elevated temperature during this step, but preferred temperatures range from about 120° C. to about 220° C. In certain embodiments, the mixture can be heated to more than about 110° C., more than about 120° C., more than about 130° C., more than about 140° C., more than about 150° C., more than about 160° C., more than about 170° C., more than about 180° C., more than about 190° C., more than about 200° C., more than about 210° C., more than about 220° C., more than about 230° C., more than about 240° C., or more than about 250° C.

During the step of heating, the composition of the dilute salt solution, acid/amine complex and water immiscible solvent can mixed to facilitate the transfer of amine from dissociated acid/amine complex to the solvent phase. For example, conventional methods and equipment for mixing liquids can be employed. Suitable mixing processes and equipment are described below in the Examples.

Upon heating, the acid and amine from the acid/amine complex dissociate, and the dissociation can occur very rapidly, typically in a few minutes. Typically, upon heating to a given temperature, the products can be sampled as soon as the temperature is reached, and then at various subsequent times. If the composition does not change further after the first sampling, the dissociation was essentially complete at the first sampling. In certain embodiments, the mixture may be heated for at least about 5 seconds or at least about 1, 2, 3, 4, 5, 6, 7, 8, 9, 10, 15, 20, 25, 30, 45 or 60 minutes. In other embodiments, the mixture may be heated for over one hour.

After the dissociation of the acid/amine complex, in the presence of a water immiscible solvent, two phases (an aqueous phase and a solvent phase) will form upon settling. The aqueous phase will include undissociated acid/amine complex and free acid and the solvent phase will include amine. The settling is preferably conducted while the composition is still at the elevated temperature. The two phases can be separated by any suitable means such as decantation, centrifugation, settling or combinations thereof. For example, any process known in the art for liquid-liquid extraction can be used to carry out the process including continuous processes such as mixer/settlers, a packed column, a pulsed column, an agitated column or centrifugal extractors. A batch process can also be used.

The process is preferably carried out in a number of stages as is well known in the art of liquid-liquid extraction. Specifically, the process can be carried out in a one stage contactor or a multi-stage cascade can be used to provide high conversion and recovery of the amine and of the acid. The solvent and aqueous streams in such a process can move cocurrently or counter currently through the cascade. For the same number of stages, a counter current configuration will require less solvent than a cocurrent configuration to achieve the same amount of extraction. Similar to a common extraction cascade, a higher solvent to feed ratio and/or higher number of contacting stages will achieve a higher percent of total recovery of the amine into the solvent phase. In addition, higher temperatures can enhance recovery and allow for use of fewer stages to achieve similar recoveries. One skilled in the art can optimize the ratio of solvent to feed and the number of stages in order to reach the desired percent of amine recovery, while minimizing the operating and capital cost.

In some embodiments, separation is conducted in more than one stage, more than two stages, more than three stages and in a preferred embodiment is conducted in three stages.

In other embodiments, the recovery of amine in the solvent from the acid/amine complex can be at least about 80%, at least about 90%, at least about 95%, at least about 97%, at least about 98% or at least about 99% by weight.

The solvent phase comprising the amine is typically virtually water free and the solution of amine typically does not exhibit any obvious breakdown products. After separation of the solvent phase and the aqueous phase, the amine is found almost exclusively in the solvent phase, wherein about less than about 10% of the acid in the system is in the solvent phase, less than about 5%, less than about 0.5% or about 0.1% of the acid in the system is present in the solvent. The organic acid, which is in its protonated or free form, is found almost exclusively in the water phase along with undissociated acid/amine complex.

After the majority of the acetic acid has been freed from the amine complex, the organic acid in the aqueous phase may then be recovered by any suitable means such as distillation, reactive distillation, extraction, or reactive extraction. The organic acid, which is now protonated acid and reactive, may also be directly converted to a further product such as an ester by any suitable means such as reactive distillation or reactive extraction or any other suitable means known in the art. Because it is protonated it can also be recovered by extraction with a solvent containing an amine.

Some of the significant advantages of the present invention are that various components of the process can be recovered and recycled for reuse in the process. Since the amine is typically a high boiling compound, a solvent selected with a lower boiling point can easily be separated from the amine by simple distillation. Solvent selection on the basis of boiling point relative to the amine can be optimized by criteria known to those skilled in the art.

The amine from the solvent phase can be recovered and used as the amine that is introduced with $CO_2$ to a dilute salt solution to form an acid/amine complex and the insoluble carbonate salt.

A further embodiment of the present invention is a method for the recovery of an organic acid from an amine salt of the organic acid. This method includes heating an aqueous solvent that includes the amine salt of the organic acid in the presence of a water immiscible solvent to thermally dissociate the amine salt of the organic acid. The water immiscible solvent is one in which the organic acid is immiscible. In this manner, an amine and an organic acid are formed. Other aspects of this embodiment are described above in connection with other embodiments of the invention.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

The following examples are provided for the purpose of illustration and are not intended to limit the scope of the present invention.

EXAMPLES

Example 1

This example illustrates that an amine, tributylamine (TBA), preferentially reports to the hydrocarbon phase in a two phase system of aqueous acetic acid/TBA complex and acetic acid solution and a normal hydrocarbon solvent of heptane.

1,750 mL of an aqueous feed of 5% by mass acetic acid stream was combined with 1,283 mL of heptane into a 2 gallon high-pressure agitated Parr reactor. This solution was then heated to 200° C. and agitated on high. When the desired temperature was reached, TBA was added to the system in discreet amounts of 14.93, 30.27, 96.98, 97.29, 97.09, 97.04, 97.21 and 97.4 gram additions. A high pressure piston driven chromatography pump (Eldex) was used to add the TBA into the pressure vessel when the vessel reached temperature and pressure. After each of these eight additions, the system was allowed to agitate on high for a time period of 30 minutes. After each agitation period, the system was allowed to settle and phase separate for five minutes. After each settling period, samples were taken through a sample port and heat exchanger from the organic and aqueous phases to determine the TBA composition in each phase. In summary, eight TBA additions were made and two samples from each phase were taken at those times. Samples were taken from ⅛" stainless steel dip tubes that extended through the top of the high pressure mixer into each phase. The tubing was coiled and inserted into a pipe jacket with circulating cooling water, such that adequate cooling was available to chill the samples to room temperature before leaving the pressurized space. The hold-up volume in the sample tubing and cooling unit was 7 mL. A total of four 10 mL samples were taken at each condition so that the sample tube could be adequately cleared of material from previous samples. Finally, a fifth 10 mL sample was taken and used as the sample to represent the equilibrium mixture in the Parr. All purge samples and the final samples were analyzed for the presence of TBA and used to close TBA mass balance on the experiment. In total, 628.1 grams of TBA were added to the experiment and essentially 100% of the TBA was accounted for in the samples and in the final amount of TBA left in the system. A calibrated GC (Agilent) with FID detector and Agilent DB5MSUI ultra-inert column were used to determine the TBA composition of each sample. The equilibrium compositions of the TBA in each phase, as measured from the fifth sample taken at each condition, are shown in Table I below.

TABLE 1

| TBA Addition | mass % TBA in the AQ phase | % mass TBA Solvent |
| --- | --- | --- |
| 1 | 0.32% | 0.8% |
| 2 | 0.67% | 4.2% |
| 3 | 1.07% | 13.8% |
| 4 | 1.60% | 22.6% |
| 5 | 1.82% | 28.9% |
| 6 | 2.00% | 35.2% |
| 7 | 2.19% | 40.3% |
| 8 | 2.28% | 44.7% |

FIG. 1 displays this data graphically.

Figure 2:
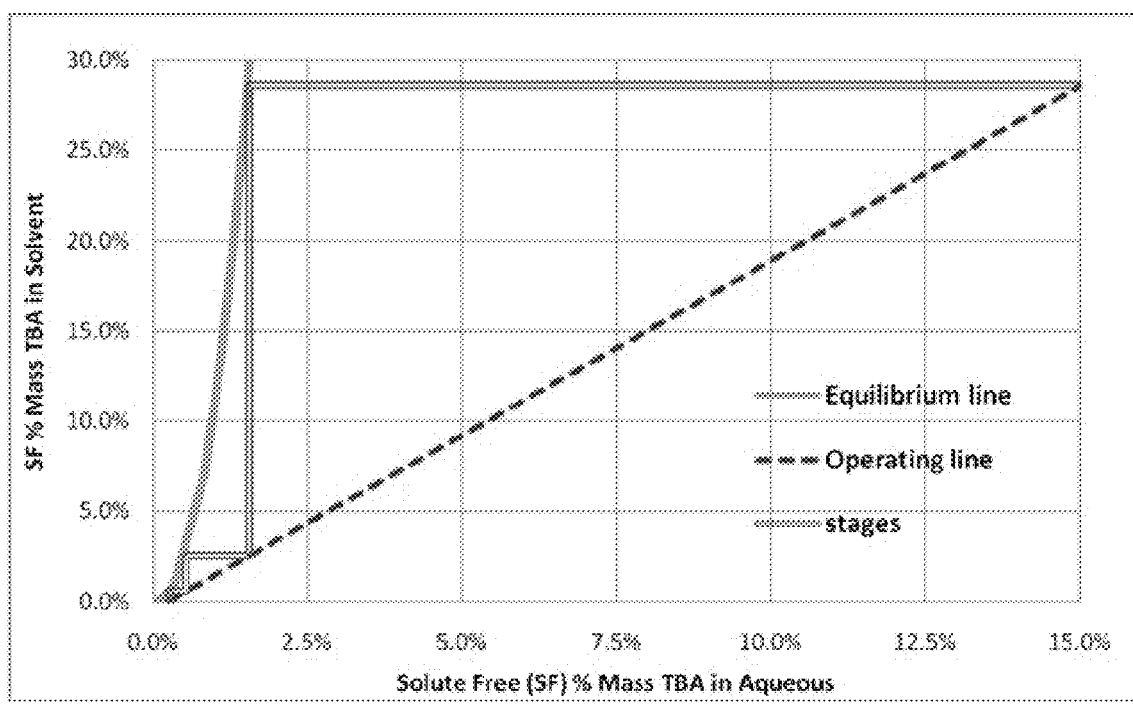
FIG. 2 is a McCabe-Thiele diagram illustrating a countercurrent three equilibrium-stage cascade.

FIG. 2 is a McCabe-Thiele diagram illustrating a counter-current three equilibrium-stage cascade. The equilibrium curve is based on equilibrium experimental data taken at 200° C. as described in this Example. In the design represented by FIG. 2, the solvent to feed ratio was set to 0.45 and the amount of TBA extracted into the solvent to 98.25%. The number of equilibrium stages was calculated by a procedure that is familiar to those skilled in the art.

Example 2

This example illustrates that equilibrium of TBA complex and acid aqueous phase and organic phase containing TBA is reached quickly in a two phase system and that two different solvents, heptane and dodecane, have similar equilibrium curves.

Using the same apparatus as in Example 1, 1,400 mL of 5% by mass acetic acid stream was combined with 3,742 mL of dodecane in a 2 gallon agitated pressure vessel. This solution was heated to 200° C. A total of five TBA additions of 50, 150, 300, 400 and 600 grams of TBA were pumped into the mixing vessel. After each condition, time course samples were taken to determine if the mixture was at equilibrium. Additions were agitated on high for 1, 5 and 30 minutes. After each agitation period, the mixture was allowed to settle for five minutes before the sample was taken. For this experiment 50 mls of material was taken out to purge the sample tube before taking the 10 ml sample.

Figure 3:
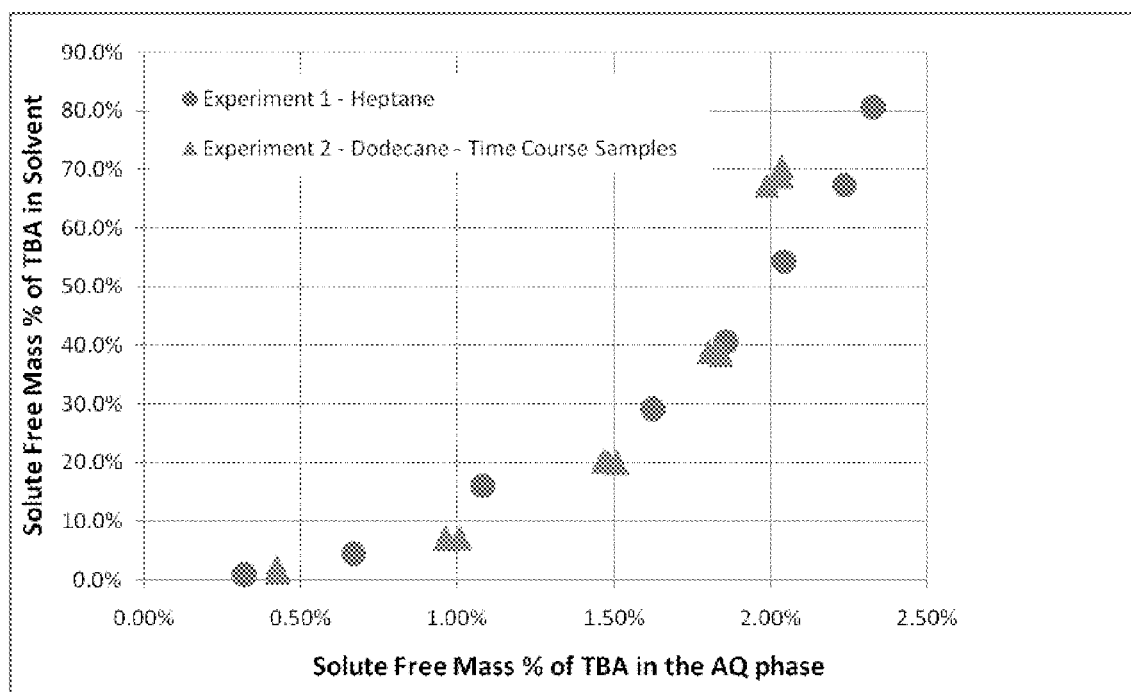
FIG. 3 is a graph illustrating the solute free mass percent of TBA in solvent and the solute free mass percent of TBA in 50 g/L of acetic acid.

The results are shown graphically in FIG. 3. Very little variation was seen in the three samples taken at each TBA loading; all these points nearly overlap for each condition. The equilibrium curve was also very similar for these two solvents.

Example 3

This example illustrates the effect of temperature on the equilibrium concentration of TBA in a two phase system of aqueous acetic acid/TBA complex and acetic acid solution and a normal hydrocarbon solvent of heptane.

Figure 4:
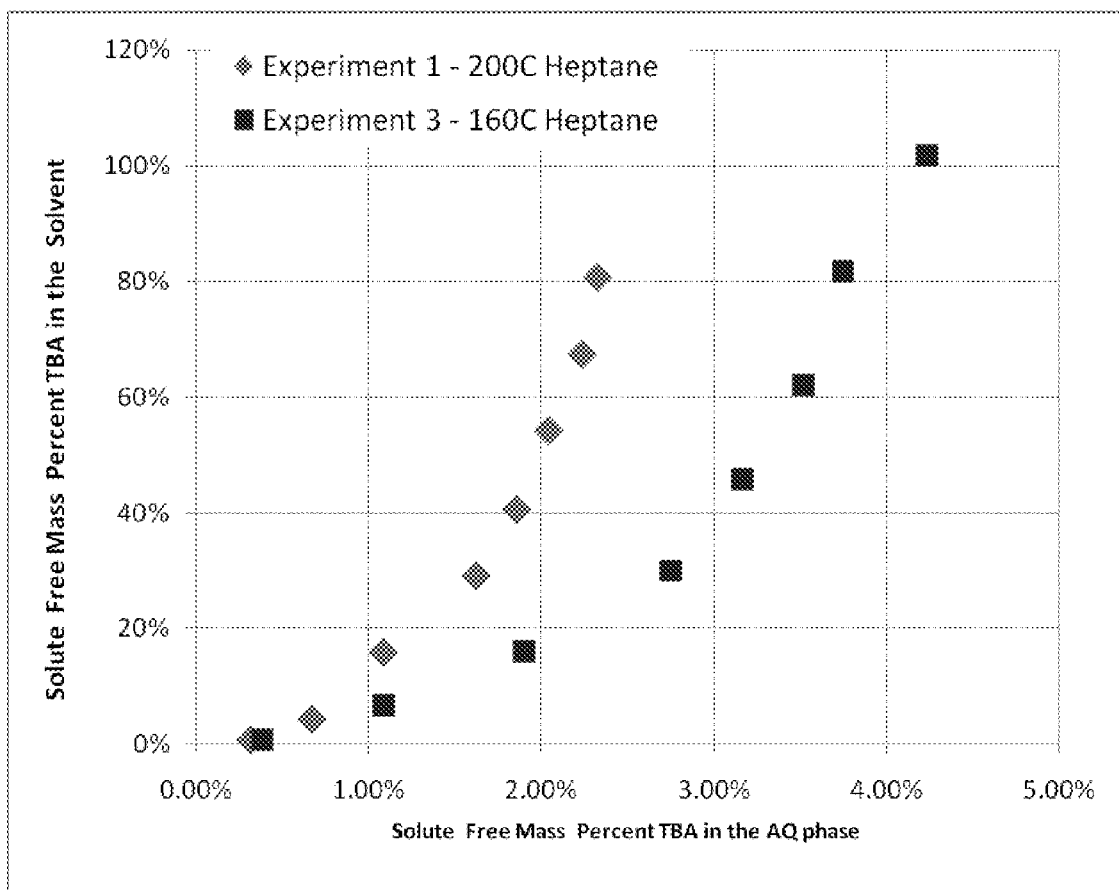
FIG. 4 is a graph illustrating the mass percent of TBA in solvent and aqueous solutions at 160° C. and 200° C.

1,750 mL of a 5% by mass acetic acid stream was brought into contact with 1,282 mL of heptane. The mixture was heated to 160° C. in the 2 gallon pressure reactor used in Example 1. Eight TBA additions were made in very nearly the same quantities as before in Example 1. The concentrations of TBA measured in the samples taken are shown in Table 2 below. A comparison of Example 1 and Example 3 illustrates the effect that temperature has on the concentration equilibrium curve of TBA in the two liquid phases, which is shown graphically in FIG. 4.

TABLE 2

| g TBA added | Mass TBA AQ % | Mass % TBA Solvent |
|---|---|---|
| 15.4 | 0.40% | 0.8% |
| 30.07 | 1.05% | 6.3% |
| 97.25 | 1.78% | 13.7% |
| 97.15 | 2.56% | 23.0% |
| 97.07 | 3.07% | 30.6% |
| 97.17 | 3.21% | 37.8% |
| 97.39 | 3.61% | 44.3% |
| 97.18 | 3.99% | 50.3% |

Example 4

This example illustrates the effect of solvent to aqueous (or feed) flow ratios, agitation rate, total flow rate and temperature on the present invention in a pilot unit.

Figure 5:
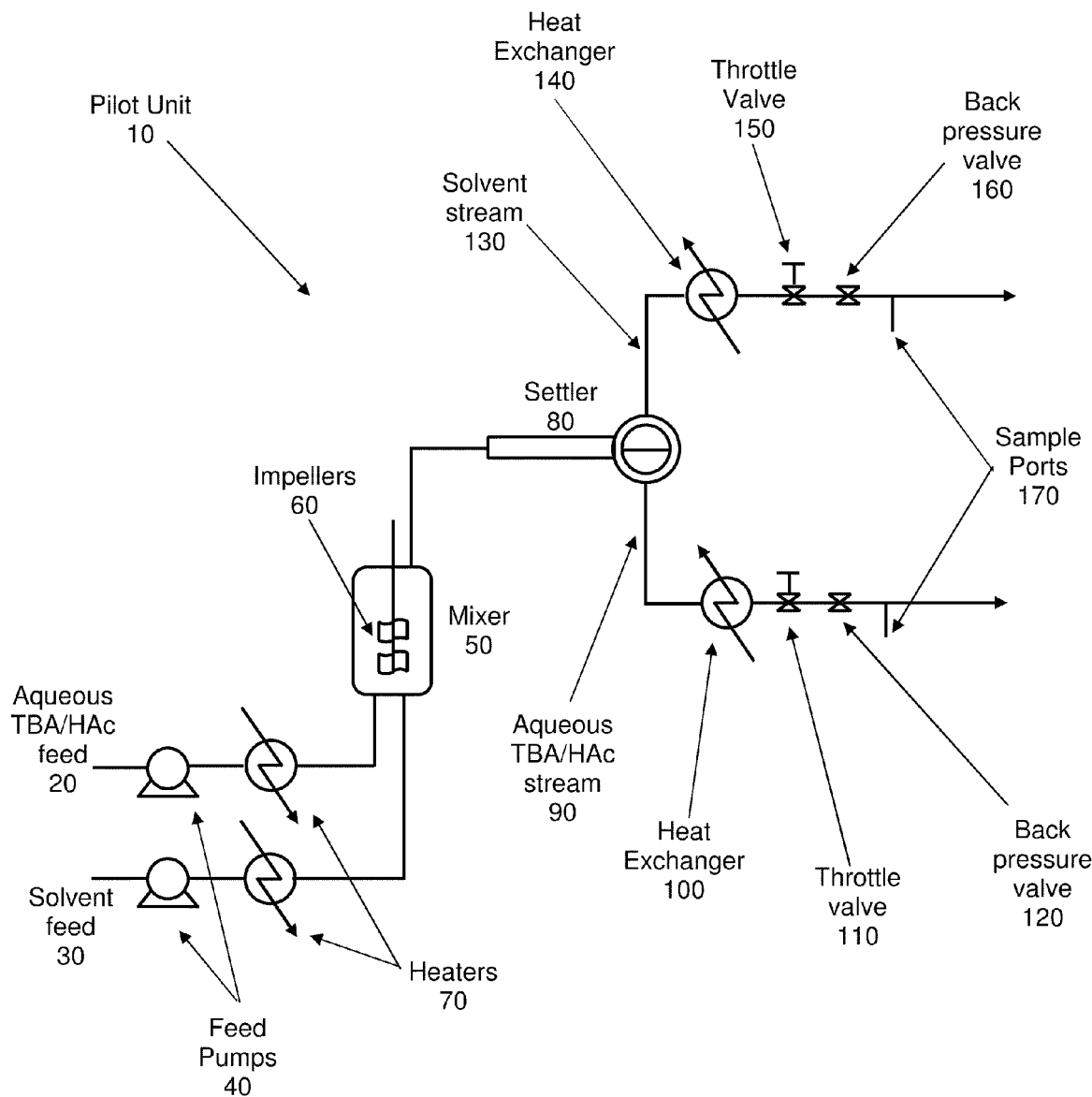
FIG. 5 is a schematic of a pilot unit for practicing the present invention

With reference to FIG. 5, a pilot unit 10 was assembled to generate design data for a commercial extraction process using the present invention. The unit was assembled such that an aqueous stream of acetic acid and TBA, up to a 1:1 molar concentration of TBA, could be heated and brought into contact with a water insoluble solvent stream that was heated separately. Dodecane was chosen as the solvent, because it has a relatively low vapor pressure at 200° C. and is less flammable than lower molecular weight alkanes. The aqueous stream 20 and solvent stream 30 were fed independently via feed pumps 40 to a 200 mL mixer (Parr reactor) 50 with a length to diameter (L/D) ratio of 2, and two turbine impellers 60 were used with an L/D ratio of 0.65. The aqueous stream 20 and solvent stream 30 were heated via heaters 70 before entering the mixer 50. The agitator speed was variable from 40 RPM to 1500 RPM. The aqueous stream 20 and solvent stream 30 were fed to the bottom of the mixer 50. The mixer 50 had a port for take-off of the mixture to a settler 80 out of the top of the mixer 50. The settler 80, comprising a section of high pressure tubing, had a volume of 180 mL and contained a high pressure sight glass such that the interface level of the solvent and aqueous phases could be observed and controlled. An aqueous stream 90 flowed out of the bottom of the settler and passed through a cooling heat exchanger 100, then through a throttle valve 110 and back pressure valve 120. Similarly, the solvent stream 130 was taken from the top of the settler 80 through a cooling heat exchanger 140, throttle valve 150 and back pressure valve 160. Sample ports 170 were installed after the back pressure valves 120 and 160, such that various conditions could be tested and samples could be taken of each phase at those conditions. The throttle valves 110 and 150 were used to control the level of the interface in the settler by adjusting the rate at which the respective phases were removed from the settler 80.

Figure 6:
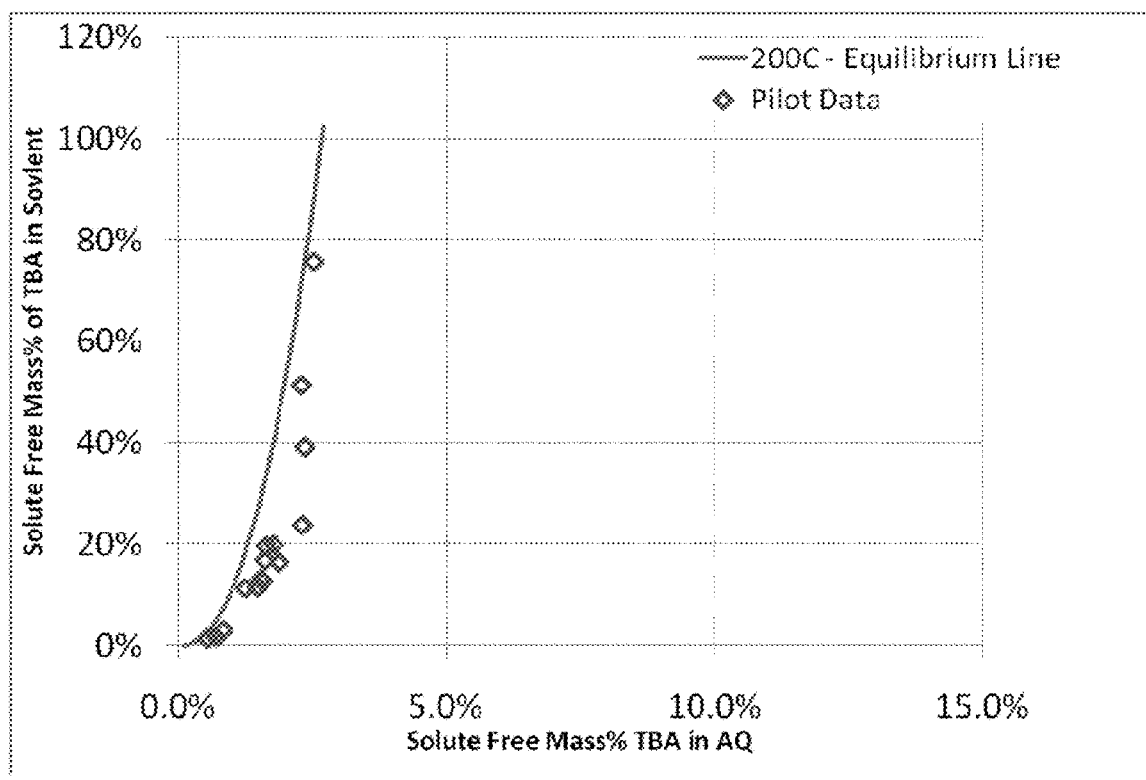
FIG. 6 is a graph illustrating pilot data collected of the SF mass percent of TBA in solvent and the SF mass percent of TBA in aqueous solution.

Pilot runs were made by varying solvent to aqueous flow ratios (S/F) to the mixer, the agitation rate, the total flow rate and the temperature. Experiments were allowed to run until steady state temperatures and concentrations were reached in the solvent and aqueous streams reaching the sample ports. Experiments were run and the results of the TBA concentration in both phases were measured and compared to the equilibrium data gathered in the 2 gallon batch reactor that were run in Examples 1 and 2. Results are shown in Table 3 below, for 15 conditions that were initially tested in the pilot unit. The data is also graphically represented in FIG. 6. The equilibrium curve shown is a power fit regression of the equilibrium data from the example experiments run at 200° C. For all conditions tested in the pilot unit greater than 95% of the amount of TBA that would have been expected from the data of Example 1 had the system reached equilibrium was extracted.

TABLE 3

| S:F ratio Mass | RPM | Residence Time Reactor (min) | Residence Time Settler (min) | Reactor Temp. (C.) | Settler Temperature (C.) | Solute Free Mass % of TBA in AQ feed. | Solute Free Mass % of TBA post extraction | Solute Free Mass % of TBA in Solvent Post Extraction |
|---|---|---|---|---|---|---|---|---|
| 0.79 | 1300 | 1.6 | 1.5 | 204 | 190.2 | 2.0% | 0.55% | 1.41% |
| 0.84 | 1300 | 3.2 | 2.9 | 205 | 172.3 | 2.0% | 0.70% | 1.71% |
| 0.39 | 1300 | 1.1 | 1.0 | 203 | 189.2 | 2.0% | 0.84% | 3.06% |
| 0.53 | 1000 | 1.0 | 0.9 | 202 | 193.2 | 10.8% | 1.49% | 11.52% |
| 0.53 | 500 | 1.0 | 0.9 | 202 | 192.5 | 10.8% | 1.57% | 12.81% |
| 0.53 | 250 | 1.0 | 0.9 | 201 | 192.0 | 10.8% | 1.54% | 13.09% |
| 0.74 | 1000 | 1.3 | 1.2 | 201 | 191.0 | 10.8% | 1.26% | 11.30% |
| 0.31 | 1000 | 0.8 | 0.7 | 200 | 194.0 | 10.8% | 2.31% | 23.81% |
| 0.69 | 500 | 0.8 | 0.7 | 199 | 191.0 | 15.4% | 1.61% | 16.84% |
| 0.69 | 100 | 0.8 | 0.7 | 202 | 191.0 | 15.4% | 1.88% | 16.44% |

TABLE 3-continued

| S:F ratio Mass | RPM | Residence Time Reactor (min) | Residence Time Settler (min) | Reactor Temp. (C.) | Settler Temperature (C.) | Solute Free Mass % of TBA in AQ feed. | Solute Free Mass % of TBA post extraction | Solute Free Mass % of TBA in Solvent Post Extraction |
|---|---|---|---|---|---|---|---|---|
| 0.14 | 500 | 1.7 | 1.6 | 203 | 191.4 | 15.4% | 2.52% | 75.66% |
| 0.61 | 500 | 1.7 | 1.5 | 203 | 180.0 | 15.4% | 1.63% | 19.66% |
| 0.61 | 100 | 1.7 | 1.5 | 204 | 184.0 | 15.4% | 1.78% | 19.90% |
| 0.28 | 1000 | 1.0 | 0.9 | 204 | 180.0 | 15.4% | 2.36% | 39.09% |
| 0.21 | 1000 | 2.2 | 1.9 | 204 | 180.0 | 15.4% | 2.30% | 51.39% |

What is claimed is:

1. A method for recovery of an organic acid from a dilute salt solution comprising an organic acid salt, the cation of which forms an insoluble carbonate salt, comprising:
   a. introducing an amine and $CO_2$ to the dilute salt solution to form an acid/amine complex and the insoluble carbonate salt;
   b. heating the acid/amine complex in the presence of a water immiscible solvent to thermally dissociate the acid/amine complex, wherein the acid is immiscible in the solvent, to form a solvent phase comprising amine and an aqueous phase comprising acid; and
   c. separating the solvent phase and the aqueous phase.

2. The method, as claimed in claim 1, wherein the water immiscible solvent comprises an aromatic solvent.

3. The method, as claimed in claim 2, wherein the water immiscible solvent is selected from the group consisting of benzene, toluene, xylene, ethyl benzene, mesitylene, cumene and mixtures thereof.

4. The method, as claimed in claim 1, wherein the water immiscible solvent comprises a normal hydrocarbon solvent.

5. The method, as claimed in claim 4, wherein the normal hydrocarbon solvent is selected from the group consisting of hexane, heptane, octane, decane, dodecane, decalin and mixtures thereof.

6. The method, as claimed in claim 1, wherein less than about 1% of the acid is present in the solvent phase.

7. The method, as claimed in claim 1, wherein less than about 0.5% of the acid is present in the solvent phase.

8. The method, as claimed in claim 1, wherein less than about 0.1% of the acid is present in the solvent phase.

9. The method, as claimed in claim 1, wherein the amine is a tertiary amine.

10. The method, as claimed in claim 1, wherein the amine is a tertiary amine selected from the group consisting of tributylamine, dicyclohexyl methyl amine, di-isopropyl ethyl amine and mixtures thereof.

11. The method, as claimed in claim 1, wherein the organic acid was produced by fermentation in a fermentation medium.

12. The method, as claimed in claim 1, wherein the organic acid comprises a carboxylic acid.

13. The method, as claimed in claim 1, wherein the organic acid comprises an organic acid selected from the group consisting of acetic acid, lactic acid, propionic acid, butyric acid, caproic acid, succinic acid, citric acid, 3-hydroxypropionic acid, glycolic acid, formic acid and mixtures thereof.

14. The method, as claimed in claim 1, wherein the organic acid comprises acetic acid.

15. The method, as claimed in claim 1, wherein the amine from the solvent phase is used as the amine introduced to the dilute salt solution.

16. The method, as claimed in claim 1, wherein the step of heating further comprises mixing the solution comprising acid/amine complex and the water immiscible solvent.

17. The method, as claimed in claim 1, wherein the step of separating is selected from the group consisting of decanting, centrifugation and settling.

18. The method, as claimed in claim 1, further comprising recovering the organic acid from the aqueous phase.

19. The method, as claimed in claim 18, wherein the step of recovering is selected from the group consisting of distillation, reactive distillation, extraction, and reactive extraction.

20. The method, as claimed in claim 1, wherein the step of heating comprises heating to at least about 110° C.

21. The method, as claimed in claim 1, wherein the step of heating comprises heating to at least about 170° C.

22. The method, as claimed in claim 1, wherein the step of heating comprises heating to between about 120° C. to about 220° C.

23. The method, as claimed in claim 1, wherein the step of heating is conducted for at least about 5 seconds.

24. The method, as claimed in claim 1, wherein the step of heating is conducted for at least about 1 minute.

25. The method, as claimed in claim 1, wherein the step of heating is conducted for at least about 5 minutes.

26. A method for the recovery of an organic acid from an amine salt of the organic acid, comprising heating an aqueous solvent comprising the amine salt of the organic acid in the presence of a water immiscible solvent to thermally dissociate the amine salt of the organic acid to form an amine and an organic acid, wherein the organic acid is immiscible in the water immiscible solvent.

27. The method, as claimed in claim 26, wherein the water immiscible solvent comprises an aromatic solvent.

28. The method, as claimed in claim 26, wherein the water immiscible solvent is selected from the group consisting of benzene, toluene, xylene, ethyl benzene, mesitylene, cumene and mixtures thereof.

29. The method, as claimed in claim 26, wherein the water immiscible solvent comprises a normal hydrocarbon solvent.

30. The method, as claimed in claim 29, wherein the normal hydrocarbon solvent is selected from the group consisting of hexane, heptane, octane, decane, dodecane, decalin and mixtures thereof.

31. The method, as claimed in claim 26, wherein less than about 1% of the acid is present in the water immiscible solvent.

32. The method, as claimed in claim 26, wherein less than about 0.5% of the acid is present in the water immiscible solvent.

33. The method, as claimed in claim 26, wherein less than about 0.1% of the acid is present in the water immiscible solvent.

34. The method, as claimed in claim 26, wherein the amine is a tertiary amine.

35. The method, as claimed in claim 26, wherein the amine is a tertiary amine selected from the group consisting of tributylamine, dicyclohexyl methyl amine, di-isopropyl ethyl amine and mixtures thereof.

36. The method, as claimed in claim 26, wherein the organic acid was produced by fermentation in a fermentation medium.

37. The method, as claimed in claim 26, wherein the organic acid comprises a carboxylic acid.

38. The method, as claimed in claim 26, wherein the organic acid comprises an organic acid selected from the group consisting of acetic acid, lactic acid, propionic acid, butyric acid, caproic acid, succinic acid, citric acid, 3-hydroxypropionic acid, glycolic acid, formic acid and mixtures thereof

39. The method, as claimed in claim 26, wherein the organic acid comprises acetic acid.

40. The method, as claimed in claim 26, wherein the step of heating further comprises mixing the aqueous solvent and the water immiscible solvent.

41. The method, as claimed in claim 26, further comprising separating the aqueous solvent and the water immiscible solvent.

42. The method, as claimed in claim 41, wherein the step of separating is selected from the group consisting of decanting, centrifugation and settling.

43. The method, as claimed in claim 26, further comprising recovering the organic acid from the aqueous solvent.

44. The method, as claimed in claim 43, wherein the step of recovering is selected from the group consisting of distillation, reactive distillation, extraction and reactive extraction.

45. The method, as claimed in claim 26, wherein the step of heating comprises heating to at least about 110° C.

46. The method, as claimed in claim 26, wherein the step of heating comprises heating to at least about 170° C.

47. The method, as claimed in claim 26, wherein the step of heating comprises heating to between about 120° C. to about 220° C.

48. The method, as claimed in claim 26, wherein the step of heating is conducted for at least about 5 seconds.

49. The method, as claimed in claim 26, wherein the step of heating is conducted for at least about 1 minute.

50. The method, as claimed in claim 26, wherein the step of heating is conducted for at least about 5 minutes.

* * * * *